United States Patent
Ly (12)

(10) Patent No.: US 9,885,804 B2
(45) Date of Patent: Feb. 6, 2018

(54) DESKTOP HYPERSPECTRAL SPECTRA COLLECTION OF GEOLOGICAL MATERIAL

(71) Applicant: CGG SERVICES SA, Massy (FR)

(72) Inventor: Chi Vinh Ly, Katy, TX (US)

(73) Assignee: CGG SERVICES SAS, Massy (FR)

(*) Notice: Subject to any disclaimer, the term of this patent is extended or adjusted under 35 U.S.C. 154(b) by 0 days.

(21) Appl. No.: 14/917,044

(22) PCT Filed: Oct. 17, 2014

(86) PCT No.: PCT/EP2014/072358
§ 371 (c)(1),
(2) Date: Mar. 7, 2016

(87) PCT Pub. No.: WO2015/059058
PCT Pub. Date: Apr. 30, 2015

(65) Prior Publication Data
US 2016/0195638 A1    Jul. 7, 2016

Related U.S. Application Data

(60) Provisional application No. 61/894,108, filed on Oct. 22, 2013.

(51) Int. Cl.
*G01V 5/00* (2006.01)
*G01V 8/20* (2006.01)
(Continued)

(52) U.S. Cl.
CPC ............. *G01V 8/20* (2013.01); *G01J 3/027* (2013.01); *G01J 3/0264* (2013.01);
(Continued)

(58) Field of Classification Search
CPC ........................................................ G01J 3/02
See application file for complete search history.

(56) References Cited

U.S. PATENT DOCUMENTS

| | | | |
|---|---|---|---|
| 4,560,275 A * | 12/1985 | Goetz ................. | G01J 3/02 250/253 |
| 2004/0024069 A1* | 2/2004 | Chen .................. | A61K 31/445 514/772.3 |

(Continued)

FOREIGN PATENT DOCUMENTS

| | | |
|---|---|---|
| EP | 1862795 A1 | 12/2007 |
| WO | 2007/128833 A1 | 11/2007 |

(Continued)

OTHER PUBLICATIONS

International Search Report in related International Application No. PCT/EP2014/072358, dated Jan. 5, 2015.
(Continued)

*Primary Examiner* — Kiho Kim
(74) *Attorney, Agent, or Firm* — Patent Portfolio Builders PLLC (57) ABSTRACT

Presented are methods and systems for analyzing geological material from a well. A device for analyzing geological samples from a well includes: at least one light source configured to emit consistent plane polarized broad spectrum light towards the geological samples; a storage media configured to hold the geological samples; at least one hyperspectral camera configured to collect spectra reflected from at least one surface of the geological samples, wherein molecular vibrations are measured; a computing device configured to receive and process the collected reflected spectra; and the computing device configured to generate an output which includes at least a bulk material composition of the geological samples, wherein the device is configured to be portable to a well site.

19 Claims, 7 Drawing Sheets

(51) Int. Cl.
  *G01V 99/00* (2009.01)
  *G01N 21/65* (2006.01)
  *G01J 3/02* (2006.01)
  *G01V 8/12* (2006.01)
  *G01J 3/28* (2006.01)

(52) U.S. Cl.
  CPC ............ *G01J 3/2823* (2013.01); *G01N 21/65* (2013.01); *G01V 99/00* (2013.01); *G01J 2003/2826* (2013.01); *G01V 8/12* (2013.01)

(56) References Cited

U.S. PATENT DOCUMENTS

| | | | | |
|---|---|---|---|---|
| 2013/0100333 | A1* | 4/2013 | Awatsuji | G03H 1/0443 348/335 |
| 2013/0292307 | A1* | 11/2013 | Bamber | B07C 5/04 209/552 |
| 2013/0335817 | A1* | 12/2013 | Isobe | G01N 23/2251 359/363 |

FOREIGN PATENT DOCUMENTS

| | | |
|---|---|---|
| WO | 2011/120086 A1 | 10/2011 |
| WO | 2012/128764 A1 | 9/2012 |

OTHER PUBLICATIONS

Written Opinion of the International Searching Authority in related International Application No. PCT/EP2014/072358, dated Jan. 5, 2015.

A. Charsky et al., "Quantitative Analysis of Kerogen Content and Mineralogy in Shale Cuttings by Diffuse Reflectance Infrared Fourier Transform Spectroscopy", International Symposium of the Society of Core Analysts, Aberdeen, Scotland, UK, 27-30, 2012, SCA2012-27, pp. 1-12.

M.M. Herron et al., "Kerogen Content and Maturity, Mineralogy and Clay typing from Drifts Analysis of Cuttings or Core", SPWLA 55th Annual Logging Symposium, May 18-22, 2014, pp. 1-14.

* cited by examiner

DESKTOP HYPERSPECTRAL SPECTRA COLLECTION OF GEOLOGICAL MATERIAL

RELATED APPLICATION

The present application is related to, and claims priority from U.S. Provisional Patent Application No. 61/894,108, filed Oct. 22, 2013, entitled "Desktop Hyperspectral Spectra Collection of Geological Materal," to Chi Vinh Ly, the disclosure of which is incorporated herein by reference in its entirety.

TECHNICAL FIELD

Embodiments of the subject matter disclosed herein generally relate to methods and systems for analyzing material collected during the drilling of bore holes.

BACKGROUND

During the drilling of either vertical or horizontal wells for resource exploration and/or recovery, various drilling fluids, i.e., drilling muds, are employed to maintain well integrity and to clear the core hole of crushed material generated by the drilling process. This geological material generated by the drilling process can be analyzed to understand the structure and content of the material being drilled through.

One conventional method for analyzing the geological material includes sending core samples from a well site to an offsite device for analysis. These offsite devices are typically large and not suitable for delivery and use at most, if any, marine and/or land well sites. Some of these devices can collect and measure visible through short wave infrared light reflected off of these core samples. Prior to analyzing these core samples, various processing steps typically are required, such as, grinding the core samples down into very fine samples. Alternatively, on site analysis devices are typically limited in the scope of measurements and observations that can be taken as compared to the larger, offsite devices.

Another technology which has more recently been introduced for the analysis of core samples and cuttings is Diffuse Reflectance Infrared Fourier Transform Spectroscopy (DRIFTS). DRIFTS uses an infrared light which can be reflected off or transmitted through a prepared sample prior to the light being measured by a detector, the measurement being of total bond vibrations. Regarding the samples used in DRIFTS, the sample particle size has been reduced to reduce spectra effects.

Therefore, currently available systems and methods for analyzing the geological samples obtained from drilling have various limitations such as time delay associated with transmitting sample for analysis using an offsite device, limited capabilities from currently used on-site devices, and/or additional sample processing steps to be performed prior to being analyzed.

Accordingly, it would be desirable to provide systems and methods that avoid the afore-mentioned drawbacks.

SUMMARY

According to an embodiment, there is a device for analyzing geological samples from a well, the device includes: at least one light source configured to emit consistent plane polarized broad spectrum light towards the geological samples; a storage media configured to hold the geological samples; at least one hyperspectral camera configured to collect spectra reflected from at least one surface of the geological samples, wherein molecular bond vibrations are measured; a computing device configured to receive and process the collected reflected spectra; and the computing device configured to generate an output which includes at least a bulk material composition of the geological samples, wherein the device is configured to be portable to a well site.

According to an embodiment, there is a method for analyzing geological samples from a well, the method includes: emitting, by at least one light source, consistent plane polarized broad spectrum light towards the geological samples; holding, by a storage media, the geological samples; collecting, by at least one hyperspectral camera wherein molecular bond vibrations are measured, spectra reflected from at least one surface of the geological samples; receiving and processing, by a computing device, the collected reflected spectra; and generating, by the computing device, an output which includes at least a bulk material composition of the geological samples, wherein the device is configured to be portable to a well site.

According to an embodiment, there is a computer readable medium including computer executable instructions, wherein the instructions, when executed by a processor, implement a method for analyzing geological samples from a well, the medium including instructions for: emitting, by at least one light source, consistent plane polarized broad spectrum light towards the geological samples; collecting, by at least one hyperspectral camera wherein molecular bond vibrations are measured, spectra reflected from at least one surface of the geological samples; receiving and processing, by a computing device, the collected reflected spectra; and generating, by the computing device, an output which includes at least a bulk material composition of the geological samples.

BRIEF DESCRIPTION OF THE DRAWINGS

The accompanying drawings, which are incorporated in and constitute a part of the specification, illustrate one or more embodiments and, together with the description, explain these embodiments. In the drawings.

DETAILED DESCRIPTION

The following description of the exemplary embodiments refers to the accompanying drawings. The same reference numbers in different drawings identify the same or similar elements. The following detailed description does not limit the invention. Instead, the scope of the invention is defined by the appended claims.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

According to various embodiments described herein, methods and systems for analyzing geological samples at a well site are described. A desktop hyperspectral device can be configured to measure reflected spectra associated with molecular bond vibrations and produce an output describing the composition of the geological sample(s). This desktop device can provide more capabilities for analysis at land and/or marine well sites than conventional onsite systems currently provide. Additionally, according to an embodiment, a method for processing the geological samples does not require grinding down in size the samples prior to analysis. Therefore, fewer processing steps are performed prior to analyzing the geological samples.

Figure 1:
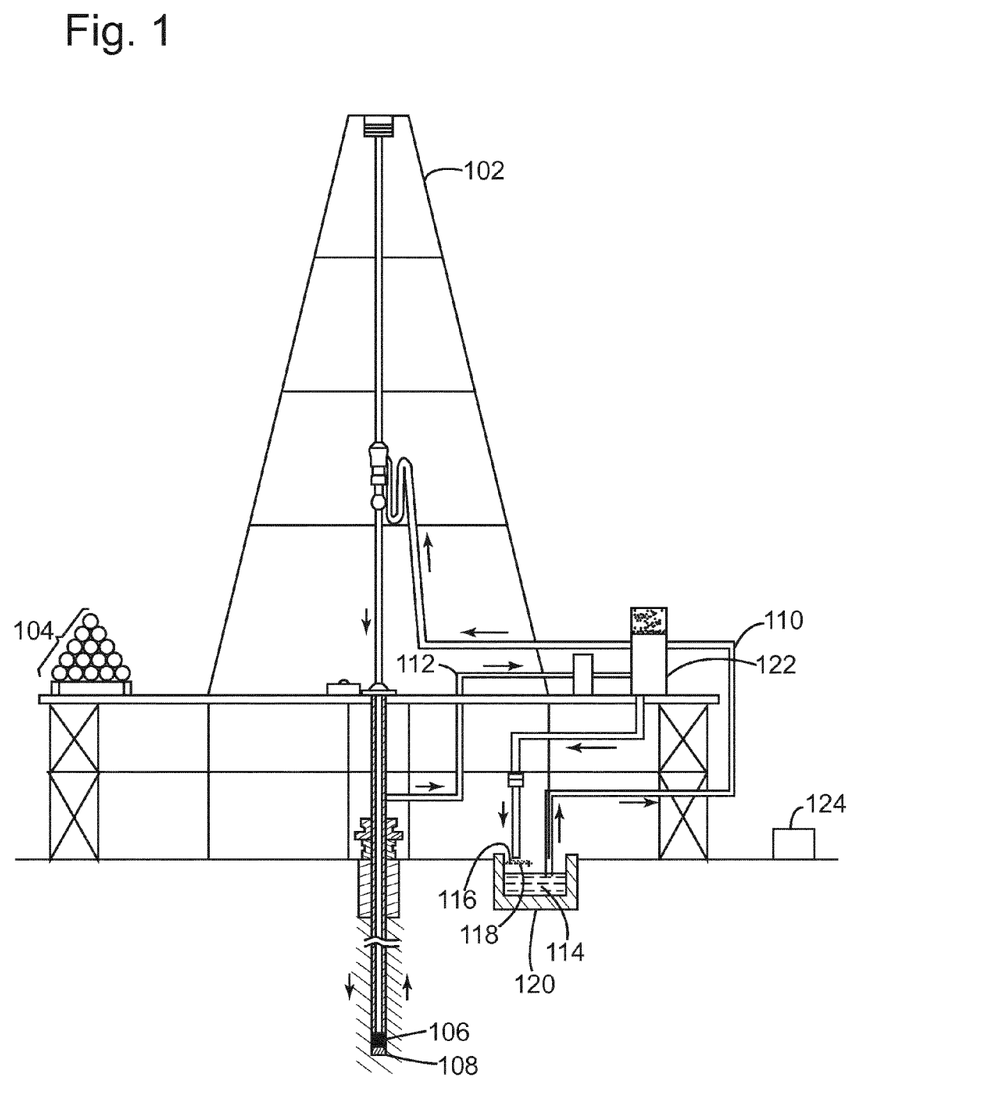
FIG. 1 depicts an onshore drilling system according to an embodiment.

Providing a context for the subsequent embodiments and looking to FIG. 1, it is known to those skilled in the art that a drilling system includes drilling derricks 102, drilling pipe 104, drill bits 106 suitable for the strata 108, supply 110 and return 112 lines for drilling mud 114 and cuttings 116 associated with the drilling operation, separation systems 118 for isolating the cuttings 116 from the drilling mud 114, a drilling mud reservoir 120 and a drilling mud pump 122. It should be noted that other aspects and configurations, known to those skilled in the art, are comprised in a drilling operation and that the described configurations are applicable to both onshore and offshore drilling operations. Drilling mud 114 circulates around the drill bit 106 collecting cuttings 116, generated by the drilling, and returns to the surface. As the drilling mud 114 arrives at the surface, a detailed mineralogical analysis of the drilling mud 114 and/or cuttings 116 can be performed. It should be noted that other aspects and configurations, known to those skilled in the art, are comprised in a drilling operation and that the described configurations are applicable to both onshore and offshore drilling operations.

According to an embodiment, analysis tools and devices can be provided at a well site, to include both land and marine applications, for analyzing geological material, e.g., drill cuttings, core samples and the like, as desired. The geological samples can be collected from a well, a bored hole, or other subsurface hole. According to an embodiment, a so-called "desktop hyperspectral device" 124 can be on location for providing additional analysis. The desktop hyperspectral device 124 uses reflected wavelengths of light, e.g., near infrared (NIR) wavelength through short wave infrared (SWIR) wavelength, to measure molecular bond vibrations of materials.

Examples of the molecular bond vibrations measured include, but are not limited to, oxygen-hydrogen (OH), water ($H_2O$), carbonate ($CO_3$), carbon-hydrogen (CH) and ammonium ($NH_4$) bonds. This allows for the detection of various substances within the geological samples, such as, clays (kaolinite group, illite, smectite group, palygorskite), phylosilicates (serpentine group, talc, pyrophilite, chlorite group), carbonates group, hydroxides (gibbsite, brucite, diaspore), some sulfates (alunite group), amiphiboles, micas, epidotes, zeolites and topaz. An example of the desktop hyperspectral device 124 will now be described.

According to an embodiment, there is a geological analysis system which includes a sample collection portion, storage media and a device, e.g., the desktop hyperspectral device 124, for the collection of spectral data. This geological analysis system is of a size which allows for deployment to both marine and land well sites as compared to most other systems which are too large to be easily deployed if at all. The system includes an instrument design which provides a capability to collect geological material at the well site, for analysis and long term storage, as well as the collection of reflectance spectra, including but not limited to visible spectra to infrared spectra, e.g., wavelengths from 380 nm to 2500 nm, from the collected geological sample's surface.

Figure 2:
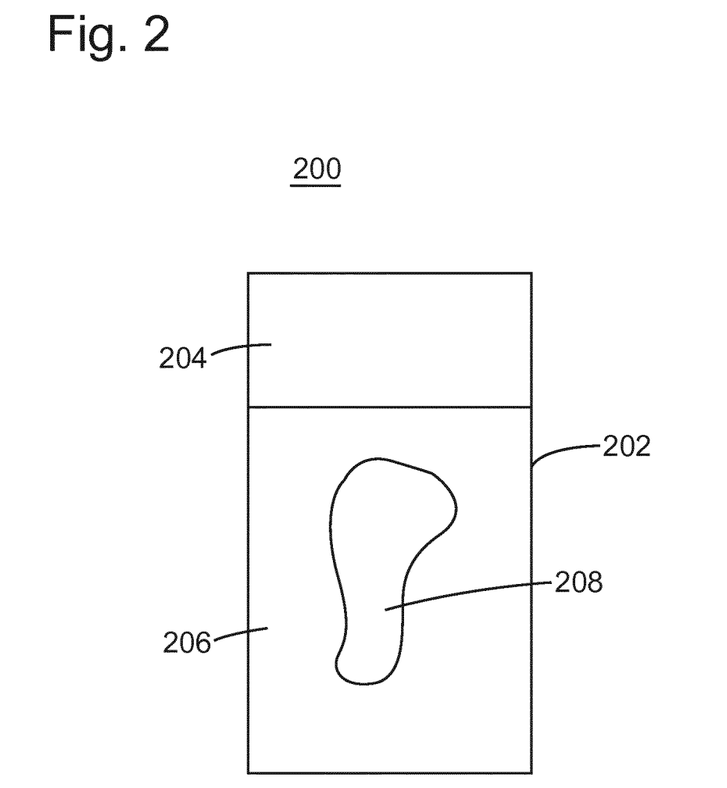
FIG. 2 depicts a storage media for use with a geological sample according to an embodiment.

According to an embodiment, as shown in FIG. 2, the storage media 200 can include a hard backing material 202, such as, cardboard or a type of plastic. The backing material can be split into two sections: a first section 204 which can be used for writing/placing sample information, e.g., a section having a coating suitable for permanent marking with a pen or other inscription device; and a second section 206 for placing the geological material, or sample, 208 to be analyzed on. The second section 206 can be coated with an adhesive material as well as having a cover section (not shown) for covering the material when placed on the adhesive this allows for adhering brecciated geological sample(s) onto the storage media 200. The cover section can be integral to the storage media 200 or a separate piece to be attached when desired. The dimensions of the storage media 200 can be such that the dimensions will be compatible with various currently used storage containers and for analysis in the desktop hyperspectral device 124.

Figure 3:
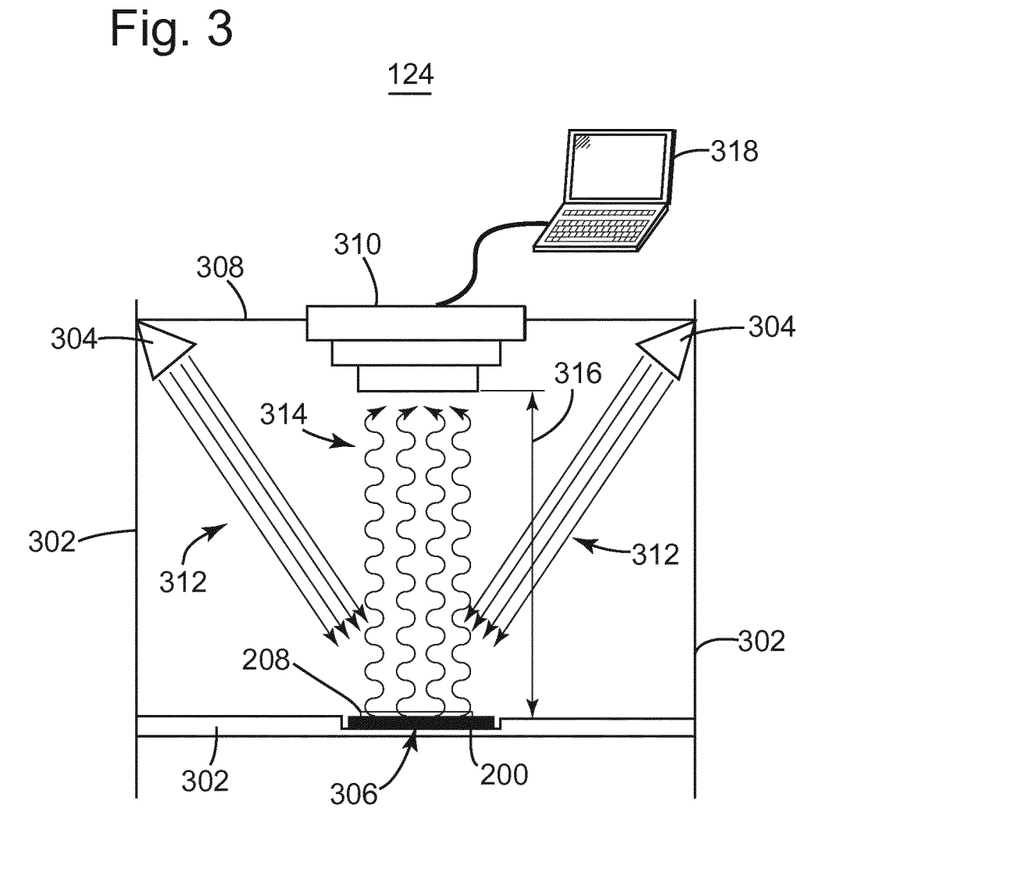
FIG. 3 depicts a hyperspectral spectra collection device according to an embodiment.

According to an embodiment, there is a desktop hyperspectral device 124 as shown in FIG. 3. The desktop hyperspectral device 124 may be open to the environment as shown here. Alternatively, the desktop hyperspectral device 124 can be closed to the environment by having, for example, an enclosed case with access provided via access ports or the like. The desktop hyperspectral device 124 includes a housing 302 which can be used to support a plurality of light sources 304 as well as having a receptacle 306 which is configured to hold the storage media 200. The housing 302 can have a roof section 308 to which one or more hyperspectral cameras 310 can be attached. Alternatively, instead of having a roof section 308, other structural members can be used from which the hyperspectral cameras 310 can be attached to.

The light sources 304 can emit consistent plane polarized broad spectrum light 312 which impacts the geological material 208 on the storage media 200. The light is then reflected off of the geological material 208 and measured by the one or more hyperspectral cameras 310 which can be configured to measure a same wavelength or different wavelengths of reflected light 314.

According to an embodiment, the location of the sample on the media storage 200 inside the receptacle 306 can be at a fixed distance 316 from the hyperspectral camera(s) 310. The distance 316 is a fixed distance which is constant between similar instruments such that the returned light intensity is the same between similar instruments, which in turn allows for repeatability between instruments for the calculated mineral amounts. The distance 316 is such that all of one surface of the storage media 200, i.e., both the first section 204 and the second section 206, are exposed to the one or more hyperspectral camera(s) 310. With the sample 208 on the storage media 200 in position in the receptacle 306, the light sources 304 can illuminate the sample 208. This results in various wavelengths of light to be reflected from the surface of the sample 208. Wavelengths of the reflected light 314 can include, but are not limited to, visible (380-800 nm), visible near infrared (400-1000 nm), NIR (900-1700 nm) and SWIR (1000-2500 nm). While FIG. 3 shows the reflectance emission to be from the storage media 200 to the hyperspectral cameras 310, it is too be understood that the reflectance from the surface of the sample 208 will be more omni-directional. The output from the hyperspectral camera(s) 310 is then transmitted via wired or wireless methods to a computing system 318 for processing.

According to an embodiment, a workflow for the processing of samples for use in the desktop hyperspectral device 124 will now be described. Initially, information such as depth obtained and other sample information can be written on or otherwise entered onto the first section 204 of the storage media 200. The sample 208 which can be a plurality of geological material, e.g., drill cuttings, can then be loaded into a sieve stack containing a coarse mesh sieve, a fine mesh sieve and a catch tray. The mesh sizes can be, but are not limited to, a 2 mm mesh size for the coarse mesh sieve and a 63 μm mesh size for the fine mesh sieve.

The sample in the sieve stack is then washed with an agent to remove any residual contamination from the drilling process. This agent could include soap, detergent, RigWash or alcohol. The output from washing the sieve stack is then separated into three groupings: oversized which is located in the coarse mesh sieve; correctly sized located in fine mesh sieve; and undersized located in the catch tray. It is to be noted that in this workflow, there is no requirement for the additional processing steps of, e.g., grinding down the sample or turning the sample into a powder as is done in various conventional methods, prior to mounting the sample for analyzing. The material in the fine mesh sieve is then further washed with water to remove the agent used for the removal of contamination from the drilling process, while the oversize and undersized materials can be returned to the original sample bag or bags. The material in the fine mesh sieve is then dried either, for example, by a heating or vacuum system, before being evenly spread onto a clean flat surface. This system allows for preparing and classifying samples at the well site.

According to an embodiment, the second section 204 of the storage media 200 is then exposed. This allows the adhesive on section 204 to then be pressed on/over the dried geological material from the fine mesh sieve which is spread out on the clean, flat surface to attach the dried geological material to the second section 204. This is performed until no more appreciable amount of material will adhere to the storage media 200, no sample material is left to be picked up, or it is determined that enough sample material is on the storage media 200.

The storage media 200 with the collected geological material sample(s) 208 is then loaded into the desktop hyperspectral device 124 by placing the storage media 200 onto the receptacle 306. The hyperspectral camera(s) 310 are then used to capture an image of the sample. If the hyperspectral camera(s) 310 are being used as a point source Charged Couple Device (CCD), with a CCD being any semi-conducting system for imaging purposes, regardless of wavelength, then the hyperspectral camera(s) 310 or sample will be faster to collect multiple point source data covering a defined area of the sample surface. If the hyperspectral camera(s) 310 being used is a CCD array then the hyperspectral camera(s) 310 will simultaneously collect point sources data over a defined area of the sample surface.

Further describing the hyperspectral camera(s) 310, there are two types of hyperspectral cameras either of which can be used according to embodiments. A first type of hyperspectral camera 310 has a single CCD which allows for measurement of one point at a time. A second type of hyperspectral camera 310 has a grid (or array) of CCDs which allow for capture of a larger area. For example, a 2×2 image generate by pixels with data in the visible spectrum (as per digital cameras) but each pixel also contains a spectrum of light, e.g., visible light to SWIR or NIR.

According to an embodiment, the reflected spectra are captured and measured, as described above, by the hyperspectral camera(s) 310. The vibrational mode which is measured by the desktop hyperspectral device 124 is primarily based upon molecular bond vibrations of the different materials in the sample 208. These molecular bond vibrations occur as a function of the wavelength(s) of light used. According to an embodiment, the wavelengths of light 312 used herein, e.g., SWIR and NIR, allow for both an improved clay speciation and an improved understanding of hydration levels of certain types of clay as compared to other, currently used measurement techniques.

The individual spectra collected and measured by the hyperspectral camera(s) 310 are then sent to a computer device or system 318 for processing. The collected spectral data generated from the hyperspectral camera(s) 310 can be used as signatures for different mineral species and sub-species. The processing includes a comparison of known spectra of known material with each pixel then assigned a definition based on this comparison with a standard spectra list. However, there are different methods available for use to identify or speciate mineral species based on the spectra data.

According to an embodiment, one method to identify or speciate mineral species based on the spectra data is a direct pattern match method which can be performed via a full spectra fit or a peak fit methodology. The full spectra fit method has the collected, measured spectra undergo a residual calculation based to determine how close the collected spectra is to a known, store library of "standard" spectra, and then classifies the spectra based on the standard spectra with the smallest residual value.

Figure 4:
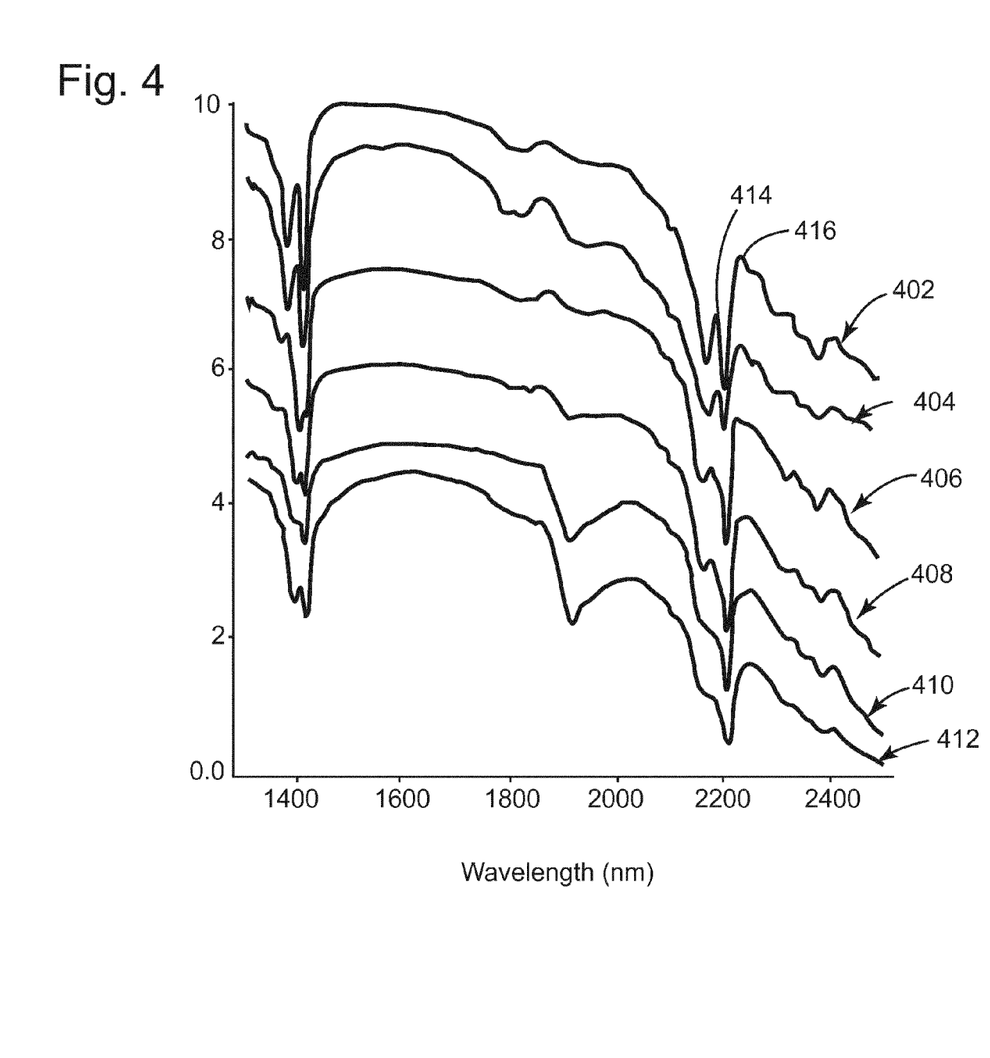
FIG. 4 shows spectrum of a mineral according to an embodiment.

An example of this can be seen in FIG. 4, which shows a plurality of spectral measurements with the Y-axis representing reflected intensity which can be measured in lumen (LUM) or as a relative percentage of known initial intensity over reflected intensity. The spectral measurement 402, for example, represents nacrite, the spectral measurement 404 represents dickite, the spectral measurement 406 represents crystalline kaolinite, the spectral measurement 408 represents crystalline kaolinite (hydrothermal), the spectral measurement 410 represents poorly-crystalline kaolinite and the spectral measurement 412 represent halloysite. This method of the pattern match with known, stored standard spectra is robust, however this method can take more time to complete and use relatively more processing power to complete analysis of each collected spectra as compared to some spectra analysis methods.

According to an embodiment, there is another method to identify or speciate mineral species based on the spectra data. This second method uses certain isolated wavelength peaks, which involves defining minerals based on specific dips and peaks in its infrared spectra, then performs a comparison of dips and peaks in the measured spectra to find the best match for the measured spectra compared to the known, stored standard spectra. For example, as shown in FIG. 4, the peaks 414 and 416 could be used to determine that the spectral measurement 402 represents nacrite. Due to scattering of the spectra when measuring an actual geological sample, as compared to using a known standard sample, the spectra data can be put into a cluster analysis framework to delineate the various mineral species and sub-species in the actual geological sample.

Figure 5:
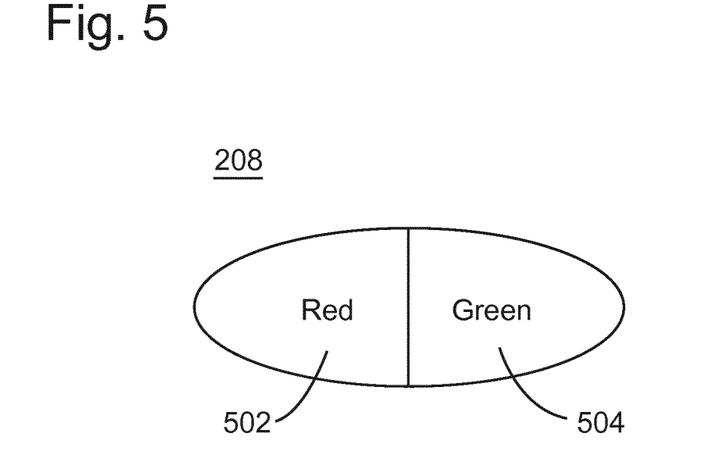
FIG. 5 illustrates a graphical output of bulk mineral composition of a geological sample according to an embodiment.

According to an embodiment, the sum of the collected and identified spectra can then be provided as a volume percent value based on the number of pixels of each material identified over the total number of pixels measured. The final output can include a bulk material composition of each sample 208 as well as a color image of the sample 208 with each color representing defined material types. For a simplified example of this output, FIG. 5 shows an oval representing sample 208 in which the sample 208 includes kaolinite and smectite. The percentage of each material can be represented by volume, e.g., the red section 502 illustrates that sample 208 is 66% kaolinite with the green section 504 illustrating that sample 208 is 34% smectite. Note that this example is very simplified and that an actual sample 208, when represented in this fashion, would be expected to show more colors representing more species and sub-species of minerals. Additionally, other graphical shapes, colors, symbols and/or styles of representation could be used here for this output.

Figure 6:
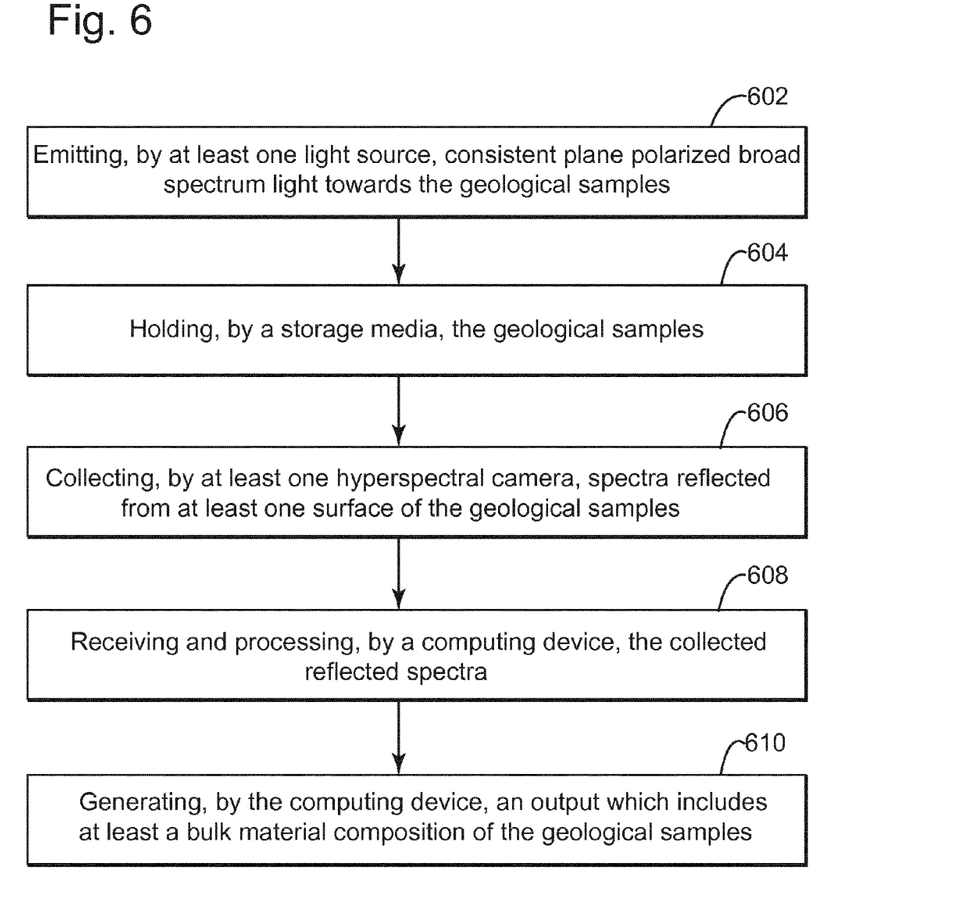
FIG. 6 depicts a flowchart of a method for analyzing geological samples according to an embodiment.

According to an embodiment, a method for analyzing geological materials from a well will now be described with respect to FIG. 6. Initially, at step 602, emitting, by at least one light source, consistent plane polarized broad spectrum light towards the geological samples; at step 604, holding, by a storage media, the geological samples; at step 606, collecting, by at least one hyperspectral camera, spectra reflected from at least one surface of the geological samples; at step 608, receiving and processing, by a computing device, the collected reflected spectra, wherein molecular bond vibrations are measured; and at step 610, generating, by the computing device, an output which includes at least a bulk material composition of the geological samples, wherein the device is configured to be portable to a well site.

Figure 7:
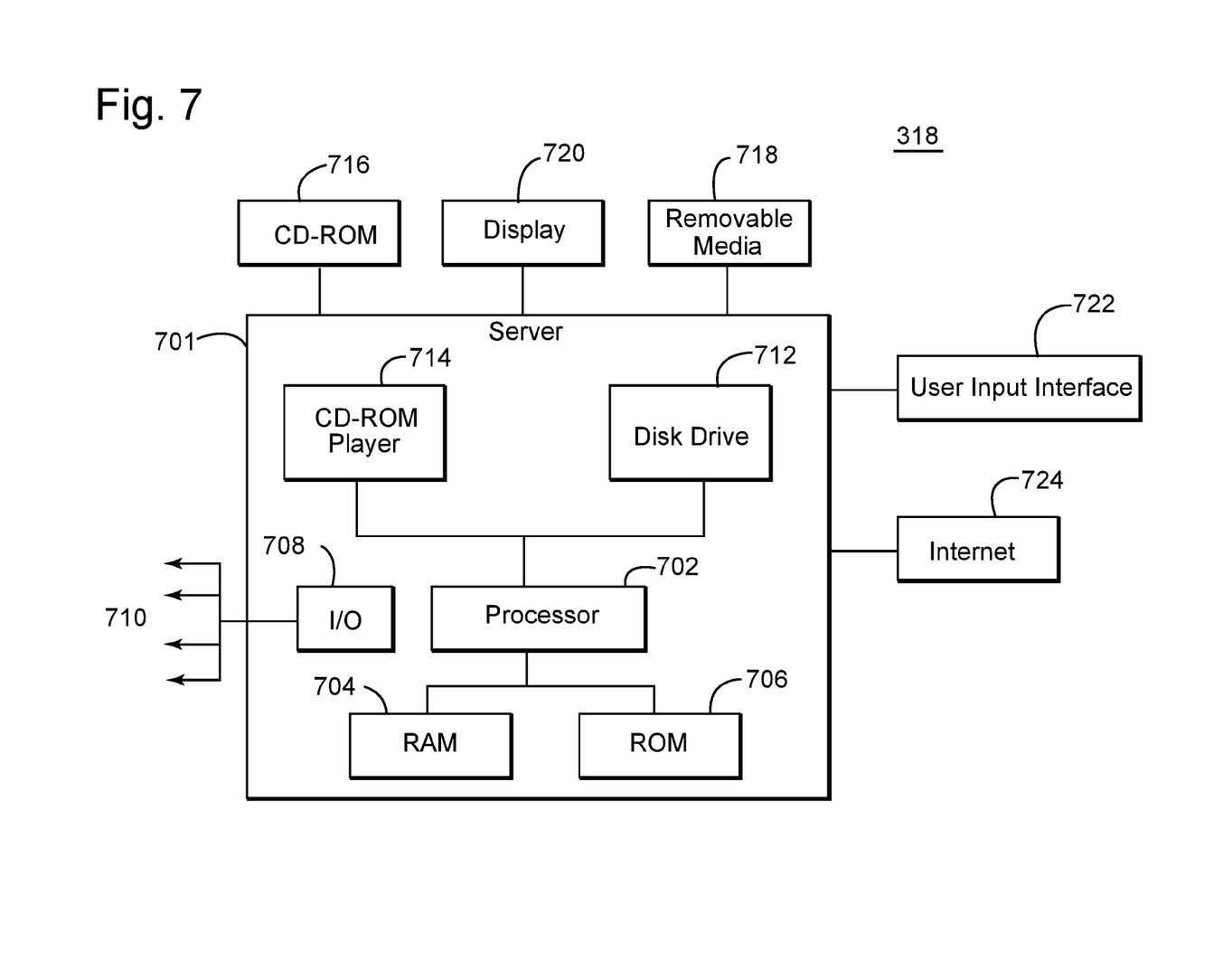
FIG. 7 depicts a computer system according to an embodiment.

An example of a representative computing system capable of carrying out the processing of the collected spectra and/or controlling various aspects of the method for analyzing geological materials from a well using the desktop hyperspectral device 124 in accordance with the exemplary embodiments is illustrated in FIG. 7. Hardware, firmware, software or a combination thereof may be used to perform the various steps and operations described herein.

The exemplary computing system 318 suitable for performing the processing and related activities, e.g., control other aspects of the desktop hyperspectral device 124 such as the lights 304 and operating of the hyperspectral camera(s) 310, described in the exemplary embodiments may include server 701. Such a server 701 may include a central processor (CPU) 702 coupled to a random access memory (RAM) 704 and to a read-only memory (ROM) 706. The ROM 706 may also be other types of storage media to store programs, such as programmable ROM (PROM), erasable PROM (EPROM), etc. The processor 702 may communicate with other internal and external components through input/output (I/O) circuitry 708 and bussing 710, to provide control signals and the like. The processor 702 carries out a variety of functions as is known in the art, as dictated by software and/or firmware instructions.

The server 701 may also include one or more data storage devices, including a hard drive 712, CD-ROM drives 714, and other hardware capable of reading and/or storing information such as DVD, etc. In one embodiment, software for carrying out the above discussed steps may be stored and distributed on a CD-ROM 716, removable memory device 718 or other form of media capable of portably storing information. These storage media may be inserted into, and read by, devices such as the CD-ROM drive 714, the disk drive 712, etc. The server 701 may be coupled to a display 720, which may be any type of known display or presentation screen, such as LCD displays, LED displays, plasma display, cathode ray tubes (CRT), etc. A user input interface 722 is provided, including one or more user interface mechanisms such as a mouse, keyboard, microphone, touch pad, touch screen, voice-recognition system, etc.

The server 701 may be coupled to other computing devices, such as the landline and/or wireless terminals via a network. The server may be part of a larger network configuration as in a global area network (GAN) such as the Internet 724, which allows ultimate connection to the various landline and/or mobile client devices.

The disclosed embodiments provide a method and system for analyzing geological material. It should be understood that this description is not intended to limit the invention. On the contrary, the exemplary embodiments are intended to cover alternatives, modifications and equivalents, which are included in the spirit and scope of the invention. Further, in the detailed description, numerous specific details are set forth in order to provide a comprehensive understanding of the embodiments. However, one skilled in the art would understand that various embodiments may be practiced without such specific details.

Although the features and elements of the present embodiments are described in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

What is claimed is:

1. A device for analyzing geological samples, the device comprising:
   at least one light source configured to emit consistent plane polarized broad spectrum light towards the geological samples;
   a storage media configured to hold the geological samples;
   at least one hyperspectral camera configured to collect spectra reflected from at least one surface of the geological samples glued on the storage media, wherein molecular bond vibrations are measured;
   a computing device configured to receive and process the collected reflected spectra; and
   the computing device configured to generate an output which includes at least a bulk material composition of the geological samples,
   wherein the device is configured to be portable to a well site, and
   the storage media has a first section for recording information associated with the geological samples and a second section that includes an adhesive for holding the geological samples on the storage media.

2. The device of claim 1, wherein the wavelengths of the reflected spectra are in a range from 380 nanometers to 2500 nanometers.

3. The device of claim 1, wherein the geological samples are collected in a mesh sieve with a mesh size of 63 micrometers.

4. The device of claim 1, wherein the at least one hyperspectral camera is configured to operate as a point source charged couple device (CCD).

5. The device of claim 1, wherein the at least one hyperspectral camera is configured to operate as an array charged couple device (CCD).

6. The device of claim 1, wherein the output further includes a color image of the geological samples with each color representing defined material types.

7. The device of claim 1, wherein the geological samples are collected from one of a well, a bored hole, or other subsurface hole.

8. The device of claim 1, wherein the molecular bond vibrations measured include the molecular bonds of at least one of oxygen-hydrogen (OH), water ($H_2O$), carbonate ($CO_3$), carbon-hydrogen (CH) and ammonium ($NH_4$) bonds.

9. The device of claim 1, wherein processing the collected, reflected spectra includes matching at least a portion of the spectra to known mineral spectra in order to determine the bulk material composition of the geological samples.

10. A method for analyzing geological samples from a well, the method comprising:
    emitting, by at least one light source, consistent plane polarized broad spectrum light towards the geological samples;
    holding, by a storage media, the geological samples, wherein the storage media has a first section for recording information associated with the geological samples and a second section which includes an adhesive for holding the geological samples on the storage media;
    collecting, by at least one hyperspectral camera wherein molecular bond vibrations are measured, spectra reflected from at least one surface of the geological samples glued on the storage media;
    receiving and processing, by a computing device, the collected reflected spectra; and
    generating, by the computing device, an output which includes at least a bulk material composition of the geological samples,
    wherein the device is configured to be portable to a well site.

11. The method of claim 10, wherein the wavelengths of the reflected spectra are in a range from 380 nanometers to 2500 nanometers.

12. The method of claim 10, further comprising:
    collecting the geological samples in a mesh sieve with a mesh size of 63 micrometers.

13. The method of claim 10, further comprising:
    operating the at least one hyperspectral camera as a point source charged couple device (CCD).

14. The method of claim 10, further comprising:
    operating the at least one hyperspectral camera as an array charged couple device (CCD).

15. The method of claim 10, wherein the output further includes a color image of the geological samples with each color representing defined material types.

16. The method of claim 10, further comprising:
    collecting the geological samples from one of a well, a borehole, or other subsurface hole.

17. The method of claim 10, wherein the molecular bond vibrations measured include the molecular bonds of at least one of oxygen-hydrogen (OH), water ($H_2O$), carbonate ($CO_3$), carbon-hydrogen (CH) and ammonium ($NH_4$) bonds.

18. The method of claim 10, wherein the step of collecting and processing, by a computing device, the collected reflected spectra further comprises:
    matching at least a portion of the spectra to known mineral spectra; and
    determining the bulk material composition of the geological samples.

19. A non-transitory computer readable medium including computer executable instructions, wherein the instructions, when executed by a processor, implement a method for analyzing geological samples from a well, the medium including instructions for:
    emitting, by at least one light source, consistent plane polarized broad spectrum light towards the geological samples;
    collecting, by at least one hyperspectral camera wherein molecular bond vibrations are measured, spectra reflected from at least one surface of the geological samples glued on a storage media that has a first section for recording information associated with the geological samples and a second section that includes an adhesive for holding the geological samples on the storage media;
    receiving and processing, by a computing device, the collected reflected spectra; and
    generating, by the computing device, an output which includes at least a bulk material composition of the geological samples.

* * * * *